United States Patent [19]

Fulconis et al.

[11] 3,935,242

[45] Jan. 27, 1976

[54] PROCESS FOR THE PREPARATION OF COLORED MANEB

[75] Inventors: Pierre Fulconis; Claude Franson, both of Marseille, France

[73] Assignee: Procida, Marseille, France

[22] Filed: July 10, 1974

[21] Appl. No.: 487,140

[30] Foreign Application Priority Data

July 13, 1973 France .............................. 73.25758

[52] U.S. Cl........... 260/429 K; 260/429 R; 424/287

[51] Int. Cl.$^2$.......................................... C07F 13/00

[58] Field of Search ................................. 260/429 K

[56] References Cited

UNITED STATES PATENTS

| | | | |
|---|---|---|---|
| 3,436,456 | 4/1969 | Louis et al. | 260/429 R X |
| 3,436,457 | 4/1969 | Louis et al. | 260/429 R X |
| 3,449,386 | 6/1969 | Chiffert et al. | 260/429 R |

OTHER PUBLICATIONS

Chemical Abstracts, Vol. 59, 8042f, (1963).

*Primary Examiner*—Helen M. S. Sneed
*Attorney, Agent, or Firm*—Hammond & Littell

[57] ABSTRACT

A process for the preparation of colored maneb comprising synthesizing maneb in a reaction media containing at least one dyestuff in solution therein.

10 Claims, No Drawings

PROCESS FOR THE PREPARATION OF COLORED MANEB

THE PRIOR ART

Maneb is the trivial name for the agricultural fungicide manganous ethylenebis-[dithiocarbamate] or [ethylenebis-(dithiocarbamato)]-manganese. The product is a fungicide currently used in agriculture to combat cryptogamic infections of plants and, in particular, of grapevines.

In the treatment of plants by pesticidal products, it is often of interest to utilize colored products which allow the obtaining of a marking on the vegetation. This marking facilitates (1) the control of the even distribution of the products during the treatment and (2) the observation of the persistance of these products on the plants, after the same had undergone exposure to weather.

Thus the problem of coloration of pesticidal products is raised for maneb, which has already been colored in various ways, in particular, blue, a color which is often preferred in the treatment of grapevines where maneb is frequently used.

Several processes for the coloring of maneb have already been proposed. These are the following:

a. Maneb can be colored by mixing and grinding it with coloring pigments which are insoluble in water and resistant to an alkaline media. However, this process presents the following inconveniences The dyes are not affixed on the active material but only mixed with it. This can produce, over several rains, a preferential washing off of the active material, with the dye only remaining on the vegetation. Thus the plants, which would still appear to be protected against fungal attack, are no longer so protected. This is a major inconvenience since maneb is often utilized in a preventative manner.

The amount of dye required in order to obtain a worthwhile coloration is also important. For example, it is necessary to add 6 percent of copper phthalocyanin to maneb in order to have a sustained blue coloration (an indication No. 452 in the universal color code by SeguyPaul Lechavalier edition). Even with 20 percent of ultra-marine blue, maneb presents only a pale blue coloration (indication No. 443 in the universal color code). Such processes are described in French Pat. No. 1,426,874, 1,514,290 and 1,562,940.

b. Maneb can be colored by mixing and grinding it with dyes which are soluble in water and resistant to an alkaline media. When the product is prepared for use in water, the dyes dissolve and are partially fixed on the maneb. For example, it is possible to obtain a blue maneb in suspension in water after having mixed and ground it with a soluble green (tetramethyldiaminotriphenyl carbenium salt) and a soluble violet (a derivative of triphenylmethane)

This process also presents inconveniences which are the following. During the preparation for use, the soluble dyes require a strong agitation for their dissolution. The absence of their dissolution creates a risk of blocking the nozzles of the spraying apparatus. The soluble dyes are only partially fixed on the plants and they are rapidly washed off by rain. The soluble dyes stain the skin and thus color in a very tenacious manner the user who effects the treatments. Such processes are described in French Pat. No. 1,402,899.

c. Another process consists, subsequent to the precipitation of maneb from the reaction media which has served in its synthesis, of fixing the dye on the maneb while it is still in suspension in the liquid phase. However, contrary to other dithiocarbamates, such as zineb which readily fix dyes when they are in suspension in a liquid phase after their precipitation, maneb only poorly fixes dyes in this fashion.

OBJECTS OF THE INVENTION

An object of the present invention is the development of a method for preparation of a colored maneb which is strongly colored and the color well fixed on the maneb and which overcomes the various inconveniences given above. Another object of the present invention is the development of a process for the production of colored maneb consisting of the steps of reacting a soluble salt of manganese with a soluble salt of ethylenebis-(dithiocarbamic acid) in the presence of a slightly basic reaction media in which said reactants are soluble, where said reaction media contains at least one dyestuff dissolved therein, and recovering, as a precipitate, a colored maneb.

A further object of the present invention is the obtaining of a strongly and well-fixed colored maneb by the above process.

These and other objects of the present invention will become more apparent as the description thereof proceeds.

DESCRIPTION OF THE INVENTION

The drawbacks of the prior art have been overcome and the above objects have been achieved by effecting the synthesis of maneb in a reaction media containing in solution at least one dye.

More particularly, the invention relates to a process for the production of colored maneb consisting of the steps of reacting a soluble salt of manganese with a soluble salt of ethylenebis-(dithiocarbamic acid) in the presence of a slightly basic reaction media in which said reactants are soluble, where said reaction media contains at least one dyestuff dissolved therein, and recovering, as a precipitate, a colored maneb; as well as the strongly and well-fixed colored maneb so produced.

In a preferred method of execution of the process, taking into account that the preferred coloration is a blue coloration, the dye used is a blue or violet dye or a mixture of blue and violet dyes. The known process for preparation of maneb consists of reacting a soluble salt of manganese with a soluble salt of ethylenebis-(dithiocarbamic acid), in an aqueous solution at a slightly basic pH. Therefore, in a non-limiting method of preparation of colored maneb, the process is characterized in that one or more of the dyes utilized are dissolved in at least one of the following phases:

a. the aqueous solution of the manganese salt;

b. the aqueous solution of the salt of the ethylenebis-(dithiocarbamic acid); or c. the water in which the reaction between the salt of manganese and the salt of the ethylenebis(dithiocarbamic acid) will be effected.

The process of the invention is advantageously operated in the following manner. One or more of the chosen dyes is dissolved in water. Then one of the reactants used [salt of manganese or salt of ethylenebis(dithiocarbamic acid)] is added to this colored solution. Then an aqueous solution of the other reactant is slowly added. The colored maneb which precipitates, is filtered, vacuum filtered and dried.

The percentage of dyestuff to be used, calculated with reference to the weight of the maneb finally obtained, can be varied over a wide range. For example, between 0.1% to 5% of dyestuff, based on the final product, may be utilized. Preferably, from 1.5% to 2.5% of soluble dyestuff is employed.

The invention, as indicated, also relates to the colored maneb characterized in that it is produced by the above-described process.

The advantages of the process and the product of the invention are the following:

1. The maneb is obtained colored directly during its manufacture and no new operation is required for its coloring;

2. The dye is fixed on the maneb particles; it thus resists repeated washings by rain, at least as long as the maneb itself, and does not give rise to being preferentially removed;

3. The percent of dyestuff employed is low and consequently the economics of the process of coloring is better than that obtained with the known process.

The differences of coloration obtained depending on whether the dyestuff was introduced before the precipitation of maneb (according to the process of the invention) or after the precipitation (according to one of the known processes and described above) is shown in the following Table I.

TABLE I

| Introduction of Dyestuff After Precipitation | | | Introduction of Dyestuff Before Precipitation | |
|---|---|---|---|---|
| Coloration of the Maneb Obtained | Color Code No. | Percentage of the Soluble Violet Dyestuff Utilized | Coloration of the Maneb Obtained | Color Code NO. |
| Pale green | 298 | 0.5 | Deep green | 404 |
| Clear green | 300 | 1.0 | Clear blue | 473 |
| Clear green | 299 | 1.5 | Deep blue | 489 |
| Clear green | 305 | 2.0 | Blue violet | 496 |

When the dyestuff is introduced into solution before the precipitation of maneb, it is fixed on the maneb, and this proportionally to the amount of the dyestuff utilized. When the dyestuff is introduced after the precipitation of maneb, a very small part of this dyestuff is fixed on the maneb and this low amount (about 0.3%) is not increased or increases only very little, even when the percentage of dyestuff utilized is increased.

The following example illustrates the process described in the present invention and the results obtained with the product prepared according to this invention. This example, however, is not to be deemed limitative in any manner.

EXAMPLE

1. Preparation of Colored Maneb 2 gm of the acid-soluble dyestuff violet fuller S4B (a dyestuff of the class of the triaminotriphenylmethanes) were dissolved in 1200 gm of water at 45°C. Then, 197 gm of a solution of the ammonium salt of ethylenebis-(dithiocarbamic acid), titrating 29:2% weight/weight was poured therein. Next 253 gm of an aqueous solution of manganese sulfate containing 290 gm/l was very slowly run in and the mixture was allowed to stand under agitation for 20 minutes.

The precipitated maneb was filtered, vacuum filtered, then dried in the presence of a stabilizer (1,8,3,6-diendomethylene-1,3,6,8-tetraazacyclodecane). The product obtained was blue (Universal color code No. 496). It titrates 92% of maneb as determined by carbon sulfide analysis and contained 0.6% of water as determined by azetropic distillation with xylene. The filtrate from which the product thus prepared was separated, contained 8 ppm of soluble dyestuff.

2. Study of the Above-Prepared Product

The product is utilized in the form of a wettable powder containing 80% active material and formulation adjuvants currently employed in the pesticidal industry. The composition thus prepared presents the following characteristics.

a. No salting out of the dyestuff when placed in suspension

The wettable powder was placed in suspension in water at a concentration of 5%. After 24 hours and filtration of the solid products, the presence of the dyestuff in an amount lower than 0.5 ppm was determined in the water of suspension. This demonstrated the solidity of the fixation of the dyestuff on the maneb.

b. Stability of the coloration of blue maneb

The coloration of the blue maneb was very stable. After 6 weeks of storage at 50°C, the coloration of the product was comparable to that of the same product stored at −20°C (same color code number as at the beginning of the storage period).

c. Chemical Stability of the Blue Maneb

The chemical stability of the maneb was not altered by the fixation of the dyestuff thereon. After 6 weeks of storage of 50°C, the loss titre was less than 5%.

d. Biological Activity

The blue maneb showed a biological activity comparable to non-colored maneb during in vitro tests against Botrytis cinerea and Fusarium roseum and during the test on tomato plants against Phytophtora infestans.

e. Resistance to Leaching by Rain

The treatements were effected on leaves of Aramon grapevines, maintained alive, at the dose of 350 gm of the formulated product per hectoliter. After the treatment, the leaves were subjected to 10 pulsed rains. The following coloration was obtained:

| Number of Rains | Leaf Coloration |
|---|---|
| 1 | pure blue, well visible |
| 2 | blue, well visible |
| 4 | clear blue, well visible |
| 6 | pale blue spots |
| 8 | blue traces, poorly visible |
| 10 | blue traces, scarcely visible |

The preceding specific embodiment is illustrative of the practice of the invention. It is to be understood, however, that other expedients known to those skilled in the art of disclosed herewin may be employed without departing from the spirit of the invention or the scope of the appended claims.

We claim:

1. A process for the production of colored maneb consisting of the steps of reacting a water-soluble salt of manganese with a water-soluble salt of ethylenebis(dithiocarbamic acid) in the presence of a slightly basic aqueous reaction media, where said reaction media contains at least one water-soluble dyestuff dissolved therein, and recovering, as a precipitate, a colored maneb.

2. The process of claim 1 wherein said at least one water-soluble dyestuff is selected from the group consisting of blue dyestuffs, violet dyestuffs and mixtures of blue and violet dyestuffs.

3. The process of claim 1 wherein the at least one water-soluble dyestuff is dissolved in an aqueous solution of the water-soluble salt of manganese.

4. The colored maneb produced by the process of claim 1.

5. The process of claim 1 wherein the at least one water-soluble dyestuff is dissolved in an aqueous solution of the water-soluble salt of ethylenebis-(dithiocarbamic acid).

6. The process of claim 1 wherein the at least one water-soluble dyestuff is dissolved in water in which the reaction between the water-soluble salt of manganese and the water-soluble salt of ethylenebis-(dithiocarbamic acid) will be conducted.

7. The process of claim 1 wherein the at least one water-soluble dyestuff is dissolved in both an aqueous solution of the water-soluble salt of manganese and an aqueous solution of the water-soluble salt of ethylenebis(dithiocarbamic acid).

8. The process of claim 1 wherein the at least one water-soluble dyestuff is dissolved in both an aqueous solution of the water-soluble salt of ethylenebis-(dithiocarbamic acid), and water in which the reaction between the water-soluble salt of manganese and the water-soluble salt of ethylenebis-(dithiocarbamic acid) will be conducted.

9. The process of claim 1 wherein the at least one water-soluble dyestuff is dissolved in both an aqueous solution of the water-soluble salt of manganese and water in which the reaction between the water-soluble salt of manganese and the water-soluble salt of ethylenebis-(dithiocarbamic acid) will be conducted.

10. The process of claim 1 wherein the at least one water-soluble dyestuff is simultaneously dissolved in (a) an aqueous solution of the water-soluble salt of manganese, (b) an aqueous solution of the water-soluble salt of ethylenebis-(dithiocarbamic acid), and (c) water in which the reaction between the water-soluble salt of manganese and the water-soluble salt of ethylenebis-(dithiocarbamic acid) will be conducted.

* * * * *